United States Patent [19]

Melquist

[11] Patent Number: 4,499,326

[45] Date of Patent: Feb. 12, 1985

[54] SELECTIVE LOW-TEMPERATURE ISOMERIZATION OF NORMAL BUTENES USING AMS-1B CRYSTALLINE BOROSILICATE MOLECULAR SIEVE

[75] Inventor: John L. Melquist, Naperville, Ill.

[73] Assignee: Standard Oil Company (Indiana), Chicago, Ill.

[21] Appl. No.: 422,822

[22] Filed: Sep. 24, 1982

[51] Int. Cl.$^3$ .............................. C07C 3/20; C07C 5/30
[52] U.S. Cl. ..................................... 585/671; 585/312; 585/322; 585/329; 585/415; 585/525; 585/531; 585/664; 585/670
[58] Field of Search ............... 585/312, 322, 329, 415, 585/417, 418, 419, 510, 520, 525, 531, 664, 666, 670, 671; 252/432

[56] References Cited

U.S. PATENT DOCUMENTS 4,268,420  5/1981  Klotz .................... 585/640
4,433,190  2/1984  Sikkenga et al. ................... 585/660
4,451,685  5/1984  Nevitt et al. ........................ 585/415

*Primary Examiner*—Delbert E. Gantz
*Assistant Examiner*—A. Pal
*Attorney, Agent, or Firm*—Wallace L. Oliver; William T. McClain; William H. Magidson

[57] ABSTRACT

A process to convert a normal butene to isomerized products comprises contacting such alkene under conversion conditions with a hydrogen form AMS-1B borosilicate catalyst composition at a conversion temperature below 250° C.

16 Claims, No Drawings

SELECTIVE LOW-TEMPERATURE ISOMERIZATION OF NORMAL BUTENES USING AMS-1B CRYSTALLINE BOROSILICATE MOLECULAR SIEVE

BACKGROUND OF THE INVENTION

This invention relates to isomerization of alkenes and more particularly relates to selective low-temperature isomerization of normal butenes using a catalyst containing hydrogen form AMS-1B crystalline molecular sieve.

Normal butenes, such as 1-butene and 2-butenes, are common refinery products which are used especially in alkylation of isobutane to form gasoline-fraction hydrocarbons. Approximately fifty percent of refinery-produced normal butenes is 1-butene. Since 2-butenes, i.e., cis-2-butene and trans-2-butene, produce an alkylate with a higher octane number than alkylate produced from 1-butene, a process to convert 1-butene to 2-butenes would be desirable. Catalyst systems have been developed for this conversion. However, there is a need for a reliable catalyst system which can be regenerated easily such as based on molecular sieves.

Zeolitic materials, both natural and synthetic, are known to have catalytic capabilities for many hydrocarbon processes. Zeolitic materials typically are ordered, porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline alumino-silicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Boron is not considered a replacement for aluminum or silicon in a zeolitic composition. However, recently a new crystalline borosilicate molecular sieve AMS-1B with distinctive properties was disclosed in U.S. Pat. Nos. 4,268,420, 4,269,813 and 4,285,919 incorporated by reference herein. According to these patents AMS-1B can be synthesized by crystallizing a source of an oxide of silicon, an oxide of boron, an oxide of sodium and an organic template compound such as a tetra-n-propylammonium salt. The process of this invention uses AMS-1B crystalline borosilicate molecular sieve.

Hydrocarbon conversion processes are known using other zeolitic materials. Examples of such processes are dewaxing of oil stock (U.S. Pat. Nos. 3,852,189, 4,211,635 and reissue U.S. Pat. No. Re. 28,398); conversion of lower olefins (U.S. Pat. Nos. 3,965,205 and 3,960,978, and European patent application No. 31,675); aromatization of olefins and aliphatics (U.S. Pat. Nos. 3,761,389, 3,813,330, 3,827,867, 3,827,868, 3,843,740, 3,843,741 and 3,914,171); hydrocracking and oligomerization of hydrocarbons (U.S. Pat. Nos. 3,753,891, 3,767,568, 3,770,614 and 4,032,432); conversion of ethane to aromatics and $C_3+$ hydrocarbons (U.S. Pat. No. 4,100,218); conversion of straight-chain and slightly branched chain hydrocarbons to olefins (U.S. Pat. Nos. 4,309,275 and 4,309,276); and conversion of $C_4$ paraffins to aromatics (U.S. Pat. No. 4,291,182).

Conversion of $C_4$ hydrocarbons using AMS-1B crystalline borosilicate under some conditions is described in commonly assigned U.S. patent applications Ser. No. 422,743 in the name of Peters and Klotz, Ser. No. 422,742 in the name of Sikkenga, Ser. No. 422,821 in the name of Nevitt, Sikkenga, and Jerome and Ser. No. 422,744 in the name of Nevitt and Jerome, all filed of even date herewith and all incorporated by reference herein.

The improvement described herein is the discovery that use of a catalyst formulation containing AMS-1B crystalline borosilicate molecular sieve at low conversion temperatures below 250° C. selectively converts a 1-alkene, such as 1-butene, to 2-alkenes, such as 2-butenes.

A method to isomerize normal butenes such as n-butenes would be desirable and a method that would isomerize a 1-alkene to 2-alkenes without excessive losses to undesirable by-products would be especially desirable. Further, a process that converts 1-butene to more useful and valuable products such as cis-2-butene and trans-2-butene would be very advantageous.

SUMMARY OF THE INVENTION

A process to convert a substantially linear alkene, such as normal butenes, to isomerized products comprises contacting such alkene under conversion conditions with a hydrogen form AMS-1B borosilicate catalyst composition at a conversion temperature below 250° C.

BRIEF DESCRIPTION OF THE INVENTION

According to this invention, substantially linear alkene such as a normal butene is contacted with a catalyst composition containing hydrogen form AMS-1B crystalline borosilicate. It is observed from the data presented below that butenes will isomerize selectively at reaction temperatures below about 250° C. without yielding significant amounts of lighter or heavier products. Thus, even at 100° C., there is significant isomerization of 1-butene.

In this invention, conversion of substantially linear alkenes such as n-butenes over AMS-1B crystalline borosilicate catalyst is performed at temperatures below about 250° C. Converting 1-butene according to this aspect favors formation of 2-butenes over isobutylene. Use of hydrogen form of AMS-1B is preferred in such conversion in that the hydrogen form is more selective to 2-butenes than forms incorporating other ions such as nickel. It was found that converting 1-butene at temperatures from about 100° to 250° C. over the hydrogen form of AMS-1B yielded substantial quantities of 2-butenes while not producing significant quantities of isobutylene. The observed variability of product composition with respect to temperature can be used desirably in modifying product mix according to market conditions. In this aspect of the invention, conversion temperature should be from about 100° to about 250° C., and preferably between about 150° to about 200° C.

For the purposes of this invention a substantially linear alkene includes normal alkenes containing four to eight carbon atoms and at least one carbon-carbon double bond. The preferable substantially linear alkene useful in this invention is a normal butene. Mixtures of substantially linear alkenes can be used in the process of this invention.

The substantially linear alkenes, or mixtures thereof, used in the process of this invention can be in the presence of other substances such as other hydrocarbon-based molecules. Thus, a feedstream used in the process of this invention comprising a substantially linear alkene also can contain other hydrocarbons such as alkanes, methane, aromatics, hydrogen, and inert gases. A process in which partially reacted hydrocarbons are recycled will contain a mixture including alkanes, alkenes, methane and aromatics. Typically a substantially linear alkene feedstream used in this invention contains about 10 to 100 wt.% substantially linear alkene and preferably contains about 50 to 100 wt.% substantially linear alkene.

The catalyst useful in this invention is based on the crystalline borosilicate molecular sieve, AMS-1B, described in U.S. Pat. Nos. 4,268,420, 4,269,813, and 4,285,919 incorporated herein by reference. A particularly useful catalyst for this invention contains hydrogen-form AMS-1B crystalline borosilicate.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

$$0.9 \pm 0.2 M_{2/n}O : B_2O_3 : ySiO_2 : zH_2O$$

wherein M is at least one cation, n is the valence of the cation, y is between 4 and about 600 and z is between 0 and about 160.

TABLE I

| d-Spacing Å[1] | Assigned Strength[2] |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

[1]Copper K alpha radiation
[2]VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

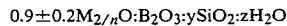

| | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blender. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible base or acid such as sodium bisulfate or sodium hydroxide. After sufficient quantities of silicic acid polymer (Ludox) are added with intensive mixing, preferably the pH is again checked and adjusted to a range of about 11.0±0.2. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25°–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

The preferable catalyst useful in this invention contains hydrogen-form AMS-1B crystalline borosilicate molecular sieve.

Ion exchange and impregnation techniques are well-known in the art. Typically, an aqueous solution of a cationic species is exchanged one or more times at about 25° to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 about 25 weight percent, depending on the process use intended. The optimum amount can be determined easily by routine experimentation.

The AMS-1B crystalline borosilicate useful in this invention can be combined with active or inactive materials, synthetic or naturally-occurring zeolites, as well as inorganic or organic materials which would be useful for binding the borosilicate. Well known materials include silica, silica-alumina, alumina, magnesia, titania, zirconia, alumina sols, hydrated aluminas, clays such as bentonite or kaolin, or other binders well known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. Catalytic compositions can contain about 0.1 wt.% to about 100 wt.% crystalline borosilicate material and preferably contain about 10 wt.% to about 80 wt.% of such material and most preferably contain about 30 wt.% to about 65 wt.% of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

In a process using this invention, a stream of an alkene, such as 1-butene, is contacted with a catalytic material-containing AMS-1B borosilicate-based catalyst. Generally, in the preferable process of this invention a linear alkene is contacted with the above-described AMS-1B borosilicate-based catalyst system in the liquid or vapor phase at a suitable reaction temperature, pressure and space velocity. Generally, suitable reaction conditions include a temperature below 250° C., a pressure of about 0.1 to about 100 atmospheres (10 to 10,000 kPa) or higher with hydrogen/hydrocarbon ratio of 0 to about 10 or higher at a weight hourly space velocity (WHSV) of about 0.1 to about 40 hr$^{-1}$. In a typical process scheme, a butene-containing hydrocarbon stream is contacted with such catalyst in a reactor at about 150° to 250° C. at a pressure of about 0.2 to about 50 atmospheres (20 to 5000 kPa) with a hydrogen/butene ratio of 0 to about 10 at a WHSV of about 0.3 to about 25 hr$^{-1}$. Preferably the butene conversion process of this invention is conducted at about 150° to about 200° C. at a pressure of about 0.3 to about 1.5 atmospheres (30 to 150 kPa) with a hydrogen/butene ratio of about 0 to about 6 at a WHSV of about 0.5 to about 6 hr$^{-1}$.

The hydrocarbon feed useful in this invention comprises a substantially linear alkene containing four to about eight carbon atoms. Also considered a linear alkene for purposes of this invention is a compound containing a linear alkene segment with four to about ten carbon atoms. It is believed that long chain linear alkenes and compounds containing linear alkene segments or a portion of such alkene or segment may penetrate the molecular sieve structure to contact a catalytic site. Thus, the entire molecule need not be small enough to fit entirely within the cavities of the molecular sieve. The preferable feed contains predominantly linear butene although typically minor amounts of other C$_4$ hydrocarbon as well as lighter components may be present. The hydrocarbon feedstream may be diluted with up to about 50 mole % inert gas such as nitrogen or helium.

This invention is demonstrated but not limited by the following Examples.

EXAMPLES 1-15

An AMS-1B borosilicate molecular sieve was prepared according to the teachings of U.S. Pat. No. 4,269,813. A two cubic centimeter sample of 50 wt.% AMS-1B crystalline borosilicate molecular sieve containing 0.4 wt.% boron incorporated in a matrix of gamma alumina crushed and sieved to 30/50 mesh (U.S. Sieve Series) was placed in a one-half inch (outside diameter) by 24 inch glass reaction tube where it was supported on a ground glass frit. Before use the AMS-1B-containing catalysts were heated to 566° C. for 16 to 64 hours. A glass wool plug was inserted on top of the catalyst and the reactor dead volume above the catalyst was filled with glass beads. The catalyst-supporting glass frit was placed approximately midway in the reactor tube. A butene feed containing 50 mole % nitrogen was contacted in the reactor with the catalyst described above. The conditions and results are summarized in Table II. The data show that 1-butene is converted in substantial yield to upgraded products including trans-2-butene and cis-2-butene. Abbreviations used in the Table are: 1-B=1-butene, t2B=trans-2-butene, c2B=cis-2-butene and iB=isobutylene. At equilibrium a product distribution (mole %) at 100° C. would be 7.0% 1-B, 65.0% t2B and 28.0% c2B; at 150° C. would be 10.2% 1-B, 60.1% t2B and 29.7% c2B; and at 250° C. would be 16.7% 1-B, 52.4% t2B and 30.8% c2B. Table III lists results from a series of comparative runs in which reaction temperature ranged from 350° to 500° C. Also two runs using isobutylene as a feed are presented. The data show that the low temperature isomerization of this invention is more selective than the comparative runs.

TABLE II

| | Examples | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Reaction Conditions | | | | | | | | | | | | | | | |
| Reactant | 1-B | 1-B | 1-B | 1-B | 1-B | 1-B | t2B | t2B | t2B | t2B | t2B | t2B | t2B | t2B | t2B |
| Temperature (°C.) | 100 | 100 | 100 | 150 | 150 | 150 | 100 | 100 | 100 | 150 | 150 | 150 | 250 | 250 | 250 |
| Contact Time (sec.) | 0.26 | 0.82 | 6.1 | 0.22 | 0.78 | 5.4 | 0.26 | 0.84 | 5.9 | 0.24 | 0.78 | 5.4 | 0.20 | 0.66 | 4.7 |
| Products (mole %) | | | | | | | | | | | | | | | |
| 1-Butene | 97.8 | 94.4 | 69.2 | 65.0 | 37.5 | 15.1 | 0.0 | 0.2 | 2.1 | 2.8 | 4.6 | 7.9 | 16.4 | 16.8 | 16.6 |
| trans-2-Butene | 0.8 | 2.0 | 12.3 | 16.4 | 31.1 | 49.8 | 99.6 | 99.3 | 96.8 | 93.3 | 87.4 | 73.6 | 51.7 | 51.3 | 51.0 |
| cis-2-Butene | 1.4 | 3.3 | 18.5 | 18.6 | 31.2 | 35.0 | 0.4 | 0.5 | 1.0 | 4.0 | 7.9 | 18.6 | 31.8 | 32.0 | 31.4 |
| Percent Approach to Equilibrium | 2.4 | 6.0 | 33.1 | 39.0 | 69.6 | 94.5 | 1.1 | 2.0 | 9.1 | 16.8 | 31.6 | 66.2 | 101 | 99.9 | 100 |

TABLE III

| | Comparative Runs | | | | | | | | | |
|---|---|---|---|---|---|---|---|---|---|---|
| | A | B | C | D | E | F | G | H | J | K |
| Reaction Conditions | | | | | | | | | | |
| Reactant | iB | iB | iB | iB | t2B | t2B | t2B | iB | iB | 1-B |
| Temperature (°C.) | 350 | 350 | 350 | 350 | 350 | 350 | 350 | 100 | 100 | 500 |
| Contact Time (sec.) | 0.57 | 0.18 | 0.63 | 3.7 | 0.17 | 0.55 | 3.8 | 0.23 | 8.4 | 0.14 |
| Products (wt. %) | | | | | | | | | | |
| Ethylene | 0.5 | 0.05 | 0.8 | 0.3 | 0.08 | 0.3 | 0.6 | 0 | 0 | 0.6 |
| Propylene | 12.8 | 7.1 | 9.1 | 10.2 | 15.3 | 17.1 | 11.4 | 0 | 0 | 8.8 |
| Isobutane | 4.3 | 0.4 | 0.9 | 2.8 | 0.3 | 1.0 | 3.2 | 0 | 0 | 0.4 |
| n-Butane | 0.5 | 0 | 0 | 0.4 | 1.3 | 1.5 | 2.2 | 0 | 0 | 0.8 |
| 1-Butene | 2.9 | 2.5 | 2.8 | 2.7 | 11.1 | 4.8 | 2.6 | 0 | 0 | 16.6 |
| Isobutylene | 13.6 | 71.1 | 51.9 | 20.2 | 8.8 | 12.7 | 10.5 | 100 | 100 | 23.0 |

TABLE III-continued

| | | | | | | | | | | |
|---|---|---|---|---|---|---|---|---|---|---|
| trans-2-Butene | 6.2 | 5.3 | 5.9 | 5.9 | 21.7 | 9.7 | 5.6 | 0 | 0 | 21.6 |
| cis-2-Butene | 4.3 | 3.6 | 4.0 | 4.1 | 15.2 | 6.7 | 3.8 | 0 | 0 | 16.4 |
| Liquids | 55.0 | 10.0 | 25.0 | 54.0 | 26.0 | 46.0 | 60.0 | 0 | 0 | 12.0 |
| Results | | | | | | | | | | |
| Conversion to non-$C_4$ Olefins (wt. %) | 73 | 18 | 35 | 67 | 43 | 66 | 78 | 0 | 0 | 22 |
| Isobutylene Yield (wt. %) | — | — | — | — | 8.8 | 13 | 10 | — | — | 23 |
| n-Butenes Yield (wt. %) | 13 | 11 | 13 | 13 | — | — | — | 0 | 0 | — |
| Propylene Yield (wt. %) | 13 | 7.1 | 9.1 | 10 | 16 | 17 | 11 | 0 | 0 | 8.8 |

| | Comparative Runs | | | | | | | | | |
|---|---|---|---|---|---|---|---|---|---|---|
| | L | M | N | O | P | Q | R | S | T | U |
| Reaction Conditions | | | | | | | | | | |
| Reactant | 1-B | 1-B | n-butane | iB | iB | iB | iso-butane | t2B | t2B | t2B |
| Temperature (°C.) | 500 | 500 | 500 | 500 | 500 | 500 | 500 | 500 | 500 | 500 |
| Contact Time (sec.) | 0.46 | 3.1 | 3.2 | 0.14 | 0.46 | 3.0 | 3.1 | 0.12 | 0.47 | 3.4 |
| Products (wt. %) | | | | | | | | | | |
| Ethylene | 2.0 | 7.5 | 0 | 0.07 | 0.5 | 3.5 | 1.2 | 0.4 | 1.2 | 6.3 |
| Propylene | 23.5 | 33.7 | 0.6 | 2.6 | 12.1 | 26.3 | 0.8 | 8.7 | 19.5 | 32.9 |
| Isobutane | 1.3 | 4.6 | 98.8 | 0.3 | 1.0 | 3.1 | 0 | 0.3 | 0.8 | 2.3 |
| n-Butane | 1.3 | 3.2 | 0 | 0 | 0.4 | 1.8 | 97.3 | 0.5 | 1.0 | 2.3 |
| 1-Butene | 8.6 | 5.0 | 0 | 6.7 | 9.4 | 6.2 | 0 | 17.3 | 10.4 | 5.4 |
| Isobutylene | 18.5 | 11.9 | 0 | 73.8 | 40.4 | 16.4 | 0 | 21.3 | 20.9 | 13.1 |
| trans-2-Butene | 11.8 | 6.8 | 0.3 | 9.4 | 13.3 | 8.7 | 0 | 23.2 | 14.2 | 7.5 |
| cis-2-Butene | 8.9 | 5.2 | 0 | 7.1 | 10.1 | 6.6 | 0 | 17.4 | 10.1 | 5.6 |
| Liquids | 24.0 | 22.0 | 0 | 0 | 13.0 | 28.0 | 0 | 11.0 | 21.0 | 24.0 |
| Results | | | | | | | | | | |
| Conversion to non-$C_4$ Olefins (wt. %) | 52 | 71 | 0 | 3 | 27 | 62 | 0 | 21 | 44 | 68 |
| Isobutylene Yield (wt. %) | 18 | 12 | 0 | — | — | — | 0 | 21 | 21 | 13 |
| n-Butenes Yield (wt. %) | — | — | 0 | 23 | 33 | 21 | 0 | — | — | — |
| Propylene Yield (wt. %) | 24 | 34 | 0 | 2.6 | 12 | 26 | 0 | 8.6 | 19 | 33 |

COMPARATIVE RUNS AA-OO

A catalyst was prepared incorporating 0.04 wt.% nickel ion exchanged onto an AMS-1B crystalline borosilicate molecular sieve. Results are shown in Table IV. The data show that a nickel exchanged catalyst is less preferable than a hydrogen form AMS-1B catalyst in terms of selectivity.

TABLE IV

| | Comparative Runs | | | | | | | | | | | | | |
|---|---|---|---|---|---|---|---|---|---|---|---|---|---|---|
| | AA | BB | CC | DD | EE | FF | GG | HH | JJ | KK | LL | MM | NN | OO |
| Reaction Conditions | | | | | | | | | | | | | | |
| Reactant | 1-B | 1-B | 1-B | 1-B | 1-B | 1-B | t2B | t2B | t2B | t2B | t2B | t2B | t2B | t2B |
| Temperature (°C.) | 100 | 100 | 100 | 150 | 151 | 151 | 100 | 100 | 100 | 149 | 150 | 150 | 248 | 250 |
| Contact Time (sec.) | 0.26 | 0.92 | 6.7 | 0.25 | 0.76 | 4.5 | 0.25 | 0.76 | 5.0 | 0.23 | 0.79 | 5.2 | 0.20 | 0.69 |
| Products (mole %) | | | | | | | | | | | | | | |
| 1-Butene | 94.8 | 90.2 | 61.0 | 51.8 | 23.9 | 14.2 | 0 | 0.1 | 0.7 | 1.9 | 3.3 | 7.9 | 16.7 | 16.4 |
| trans-2-Butene | 1.8 | 3.3 | 14.6 | 20.3 | 37.8 | 50.2 | 99.5 | 99.2 | 97.8 | 95.1 | 91.0 | 71.2 | 50.6 | 50.9 |
| cis-2-Butene | 3.0 | 6.5 | 24.5 | 28.0 | 37.8 | 32.7 | 0.5 | 0.7 | 1.5 | 3.0 | 5.7 | 20.9 | 32.4 | 32.2 |
| Isobutylene | 0 | 0 | 0 | 0 | 0.6 | 2.9 | 0 | 0 | 0 | 0 | 0 | 0 | 0.3 | 0.6 |
| Percent Approach to Equilibrium | 5.6 | 10.5 | 41.9 | 53.7 | 84.7 | 95.5 | 1.4 | 2.3 | 6.3 | 12.3 | 226 | 72.4 | 104 | 103 |

What is claimed is:

1. A process to convert a normal alkene to isomerized hydrocarbons comprising contacting such alkene under conversion conditions comprising a pressure of about 0.1 to about 100 atmospheres, a hydrogen/hydrocarbon molar ratio of 0 to about 10 and a weight hourly space velocity of about 1 to about 40 hr$^{-1}$ with a hydrogen form AMS-1B crystalline borosilicate-based catalyst composition at a conversion temperature below 250° C.

2. The process of claim 1 wherein the normal alkene comprises a normal alkene having four to eight carbon atoms.

3. The process of claim 2 wherein the alkene is a normal butene.

4. The process of claim 3 wherein the normal butene is 1-butene.

5. The process of claim 3 wherein the normal butene is trans-2-butene or cis-2-butene.

6. The process of claim 1 wherein the substantially linear alkene comprises from about 10 to 100 wt.% of a feedstream contacting the catalyst.

7. The process of claim 1 wherein the AMS-1B crystalline borosilicate composition is incorporated within an alumina or silica-alumina matrix.

8. The process of claim 7 wherein the AMS-1B crystalline borosilicate content in the matrix ranges from about 10 to about 80 wt.%.

9. The process of claim 7 wherein the AMS-1B crystalline borosilicate content in the matrix ranges from about 30 to about 65 wt.%.

10. The process of claim 1 wherein the conversion temperature is about 100° to 250° C.

11. The process of claim 1 wherein the conversion temperature is about 150° to 200° C.

12. The process of claim 1 wherein the conversion conditions are a temperature of about 150° to about 250° C., a pressure of about 0.1 to about 100 atmospheres, a hydrogen/hydrocarbon ratio of 0 to about 10 and a weight hourly space velocity of about 1 to about 40 $hr^{-1}$.

13. A process to convert n-butene to a mixture comprising isomerized products comprising contacting n-butene under conversion conditions comprising a pressure of about 0.2 to about 50 atmospheres, a hydrogen/butene molar ratio of 0 to about 10, a weight hourly space velocity of about 0.3 to about 25 $hr^{-1}$ and a temperature of about 150° to about 200° C. with a catalyst composition comprising hydrogen form AMS-1B crystalline borosilicates.

14. The process of claim 13 wherein 1-butene is converted at about 150° to about 200° C. at a pressure of about 0.3 to about 1.5 atmospheres with a hydrogen/butene ratio of about 0 to about 6 and a weight hourly space velocity of about 0.5 to about 6 $hr^{-1}$.

15. The process of claim 13 wherein n-butene comprises about 10 to 100 wt.% of a feedstream contacting the catalyst.

16. The process of claim 13 wherein n-butene comprises about 50 to 100 wt.% of a feedstream contacting the catalyst.

* * * * *